US011964080B2

(12) United States Patent
Rosenørn et al.

(10) Patent No.: US 11,964,080 B2
(45) Date of Patent: Apr. 23, 2024

(54) AIR TREATMENT SYSTEM, AND A METHOD OF USING SAID AIR TREATMENT SYSTEM

(71) Applicant: Airlich IP ApS, Allerød (DK)

(72) Inventors: Thomas Rosenørn, Birkerød (DK); Andrew Butcher, Brønshøj (DK); Jonas Ingemar, København N (DK); Cecilie Litske Carstens, København V (DK)

(73) Assignee: Airlich IP ApS, Allerød (DK)

( * ) Notice: Subject to any disclaimer, the term of this patent is extended or adjusted under 35 U.S.C. 154(b) by 526 days.

(21) Appl. No.: 16/766,243

(22) PCT Filed: Nov. 19, 2018

(86) PCT No.: PCT/DK2018/050298
§ 371 (c)(1),
(2) Date: May 21, 2020

(87) PCT Pub. No.: WO2019/101276
PCT Pub. Date: May 31, 2019

(65) Prior Publication Data

US 2020/0368384 A1 Nov. 26, 2020

(30) Foreign Application Priority Data

Nov. 22, 2017 (DK) ............................ PA2017 70879

(51) Int. Cl.
*A61L 9/20* (2006.01)
*B01D 53/00* (2006.01)
(Continued)

(52) U.S. Cl.
CPC ............ *A61L 9/205* (2013.01); *B01D 53/007* (2013.01); *B01D 53/32* (2013.01);
(Continued)

(58) Field of Classification Search
CPC ............................. A61L 9/205; B01D 53/007
See application file for complete search history.

(56) References Cited

U.S. PATENT DOCUMENTS 5,225,167 A 7/1993 Wetzel
5,635,133 A * 6/1997 Glazman ................ C02F 1/325 250/436

(Continued)

FOREIGN PATENT DOCUMENTS

CN 205174608 U 4/2016
CN 106642487 A 5/2017

(Continued)

OTHER PUBLICATIONS

International Search Report andn Written Opinion Appl. No. PCTDK2018050298 dated Apr. 25, 2019.

(Continued)

*Primary Examiner* — Kevin Joyner
(74) *Attorney, Agent, or Firm* — Fox Rothschild LLP

(57) ABSTRACT

An air treatment system (1) arranged for treating polluted air ($A_{pol}$) at least by means of an air particle filter, and wherein said air treatment system comprises an air treatment unit placed upstream of the air particle filter and being arranged for directing a sub-flow ($A_{sub}$) of the polluted air ($A_{pol}$) through said air treatment unit (2) and for subjecting the sub-flow ($A_{sub}$) to a photooxidation process. The photooxidation process in the air treatment unit (2) is so efficient that the overall concentration of gas-pollution of the combined air flow $A_{com}$ is significantly reduced whereby large volumes of polluted air can be treated in a fast, inexpensive and effective manner.

14 Claims, 3 Drawing Sheets

(51) Int. Cl.

| | |
|---|---|
| ***B01D 53/32*** | (2006.01) |
| ***B01D 53/86*** | (2006.01) |
| ***B03C 3/01*** | (2006.01) |

(52) U.S. Cl.

CPC ..... *B01D 53/8668* (2013.01); *B01D 53/8675* (2013.01); *B03C 3/01* (2013.01); *A61L 2209/12* (2013.01); *A61L 2209/14* (2013.01); *A61L 2209/16* (2013.01); *B01D 2255/1021* (2013.01); *B01D 2255/802* (2013.01); *B01D 2257/106* (2013.01); *B01D 2257/708* (2013.01)

(56) References Cited

U.S. PATENT DOCUMENTS

| | | | | |
|---|---|---|---|---|
| 2002/0100878 | A1* | 8/2002 | Summers | A61L 2/10<br>250/492.1 |
| 2005/0183576 | A1 | 8/2005 | Taylor et al. | |
| 2005/0238551 | A1 | 10/2005 | Snyder et al. | |
| 2010/0307332 | A1 | 12/2010 | Yuen | |
| 2016/0271550 | A1* | 9/2016 | Law | F24F 1/0071 |
| 2017/0304472 | A1* | 10/2017 | Neister | A61L 2/10 |

FOREIGN PATENT DOCUMENTS

| | | | |
|---|---|---|---|
| CN | 206145758 | U | 5/2017 |
| EP | 0931581 | A1 | 7/1999 |
| EP | 205699982 | U | 11/2016 |
| WO | WO2004110509 | A1 | 12/2004 |
| WO | WO2005039659 | A1 | 5/2005 |

OTHER PUBLICATIONS

Written Opinion of the International Preliminary Examining Authority (IPEA) PCT/DK2018/050298 dated Nov. 26, 2019.

* cited by examiner

AIR TREATMENT SYSTEM, AND A METHOD OF USING SAID AIR TREATMENT SYSTEM

CLAIM OF BENEFIT TO PRIOR APPLICATIONS

This application is a 371 filing of International Patent Application PCT/DK2018/050298 filed Nov. 19, 2018, which claims the benefit of PA201770879 filed Nov. 22, 2017.

TECHNICAL FIELD

The present invention relates to an air treatment system, and a method of using said air treatment system.

BACKGROUND OF THE INVENTION

It is a well known problem that air in different facilities such as homes, offices or in an industrial production rooms are contaminated with undesirable compounds and/or pollutants, e.g. volatile organic compounds, allergens and microorganisms affecting the indoor air quality and accordingly the comfort and health of the occupants in said facility.

Usually the best way to address this problem is to control or eliminate the sources of pollutants, and to ventilate the facility with clean outdoor air.

Existing heating, ventilation and air conditioning (HVAC) systems are based on a combination of recycled air as well as the intake of ambient "clean and fresh" air that in reality may contain a variety of impurities and particulate matter, including pollutants, carcinogenic compounds, volatile organic compounds from vehicle exhaust, and a long list of toxic chemicals from any number of industrial sources.

In order to remove these substances said HVAC systems employ air cleaning devices such as dry electrostatic precipitators and filters that at best remove only dust particles. Such conventional HVAC systems require manual cleaning and periodic replacement of filter media, and mechanical filtration involves limited conductance and a pressure drop, necessitating large fans and accordingly requires large amounts of energy. Even though electrostatic precipitation does not cause a large pressure drop, it only removes pre-existing particles; it does not act on gas-phase pollution.

In this respect air treatment systems utilizing UV-radiation and/or ozone has proven highly advantageously. Using this technique, it is possible to sterilize the air, and attain decomposition of all organic compounds, e.g. VOCs at the same time.

Such air treatment systems are e.g. known from WO 97/34682 and WO 99/13956 in which air may be sterilized by exposing the air to UV-radiation, and organic compounds can be removed with ozone e.g. created during the UV-radiation. UV-light and ozone may be produced from the same UV-lamp, as the lamps can be arranged for emitting different wavelengths. From said patent applications, it is also known to control and regulate the ozone concentration that are emitted into the surroundings.

However, one of the main problems which such systems is that the systems are very complicated and the reaction times extremely long. Furthermore, a large numbers of UV-lamp must be applied in order to treat the air passing though the systems. This results in expensive systems, not only in equipment and installation but also in maintenance and operation.

Another problem is that the known air treatment systems often incorporate a catalytic unit, either in order to assist in the treatment of the air thereby providing a photocatalytic system, or in order to reduce the content of ozone in the treated air, e.g. by using ozone adsorbing materials or an ozone catalyst that will convert ozone into e.g. oxygen. Such catalysts will influence the air flow and provide a large pressure drop in the system, which will necessitate large fans and accordingly involve a high energy consumption.

Thus, presently there does not exist a system which is capable of cleaning large volumes of indoor air in a fast, simple and inexpensive manner. Accordingly, there exist a demand for methods and systems that effectively can reduce pollutant in the air without causing a drop in pressure, and a system that will not provide an impact on the filtration efficiency or require significant expenses or additional equipment.

SUMMARY OF THE INVENTION

Thus, it is a first aspect of the present invention to provide an air treatment method and system arranged for treating the air in a fast and effective manner, using much less energy for the treatment process compared to the traditional systems and methods.

It is a second aspect of the present invention to provide an air treatment system having a compact structure, in which the pressure drop over the system is reduced, and which can be utilized, e.g. in an existing heating and/or ventilation and/or air conditioning (HVAC) system.

It is a third aspect of the present invention to provide an air treatment system which does not require addition of expensive oxidizing agents such as hydrogen peroxide, thereby reducing both costs and space for storage facilities.

It is a fourth aspect of the present invention to provide an air treatment system arranged for removing high concentrations of pollutants at room temperatures.

It is a fifth aspect of the present invention to provide an air treatment method and system that is simple and reliable to use.

The novel and unique features whereby these and further aspects are achieved according to the present invention is by providing an air treatment system arranged for treating polluted air at least by means of an air particle filter e.g. an electrostatic precipitator, and wherein said air treatment system comprises an air treatment unit placed upstream and/or downstream of the air particle filter and being arranged for directing a sub-flow of the polluted air through said air treatment unit and for subjecting the sub-flow to a photooxidation process.

By only subjecting a sub-flow of the polluted to a photooxidation procedure, an especially simple and inexpensive system is provided. Even though the photooxidation process primarily will remove organic pollutants e.g. VOCs from the sub-flow passing though the air treatment unit, the inventors of the present invention has discovered that the photooxidation process is so efficient that the overall content of the organic pollutants of the combined air flow, i.e. in the air flow after the air treatment unit, is significantly reduced such that the air emitted form the system only contained acceptable concentrations of said pollutants.

Furthermore, as the air treatment unit only has to treat the sub-flow, the number of required UV-lamps for providing an effective photooxidation process is reduced compared to conventional systems in which the entire polluted air stream has to be treated. The system according to the present invention therefore provides a simple and inexpensive system in relation to e.g. equipment, maintenance and energy consumption.

The photooxidation process that takes place in the air treatment unit has a number of advantages. First of all, UV light from the at least one UV-lamp in the air treatment unit will in combination with natural oxygen create highly reactive radicals and potentially ozone, which oxidises the organic pollutants such as odours, solvents etc. and eliminate them in the oxidation process. In this respect photooxidation is a destruction process wherein the resultant products are carbon dioxide, water, and inert salts, and the process residuals do not require any additional treatment.

Secondly, UV-light is an energy-saving and environmentally-friendly solution and ultraviolet radiation is powerful enough to break many covalent bonds. Alone it can degrade PCBs, dioxins, polyaromatic compounds, etc.

Finally, if the UV-lamps is arranged for generating ozone, the treatment step is even more efficient since ozone is a potent oxidant. Furthermore, as the ozone may be generated by the UV-lamps, the ozone will be generated on site and no storage area is required. It is accordingly preferred in one embodiment, that the UV-lamps is arranged for operating in an UV-spectrum which produces ozone, i.e. in a UV-spectrum around 185 nm. This is especially relevant if the at least one UV-lamp is a conventional mercury lamp.

The polluted air will be treated at least by means of an air particle filter e.g. an electrostatic precipitator, that may be placed upstream and/or downstream of the air treatment unit. However, in a preferred embodiment the the sub-flow, after being subjected to a photooxidation in the air treatment unit, be combined with the polluted air that has bypassed the air treatment unit and the combined air-flow is then passed over the air particle filter that is placed after the air treatment unit seen in the flow direction. The air particle filter may be any kind of suitable filter device arranged for removing particulate material from the air flow, e.g. particulate air (HEPA) filters and/or Ultra Low Particulate Air (ULPA) that are designed to arrest very fine particles. However, in a preferred embodiment the air particle filter is an electrostatic precipitator (ESP), in which the particles will be collected by applying an electric field on the air flow. The electric field will charge the particles, causing said particles to be collected on collecting plates in the ESP, thereby purifying the gas. Such ESP systems are well known in the art and will not be discussed in further details in this application.

In a preferred embodiment the air treatment unit comprises at least one catalyst in addition to the at least one UV-lamp. Said catalyst may either be adapted for treating the air as a photocatalyst, or it may reduce the concentration of submitted ozone into the surroundings. However, irrespectively of the purpose of the catalyst, the fact that only a sub-flow of the polluted air will pass though the air treatment unit, and accordingly pass the catalyst, the overall pressure drop in the system according to the invention will be reduced or minimal.

If the catalyst is adapted for treating the air, the air treatment unit is preferably arranged as a photocatalytic unit, in which the at least one UV-lamp and photocatalyst is mutually arranged such that the catalyst will be irradiating with UV light. Although various photocatalysts may be used in the photocatalytic unit, titanium dioxide is preferred due to the fact that titanium dioxide is generally accepted as a light, strong, and anti-corrosive compound that, if scratched or damaged, will immediately restore the oxide in the presence of air or water. The photooxidation process has the advantage that it neither requires chemicals nor high temperatures, and a variety of contaminants and concentrations can be treated.

Alternatively, the catalyst is arranged for reducing the content of ozone in the treated air, e.g. by converting ozone into oxygen. Such catalysts are known in the art, and may e.g. be a substrate with a catalyst material of a type known in the art for ozone decomposition, such as a catalyst including platinum and a base metal.

The inventors of the present invention has found that if the sub-flow directed though the air treatment unit is between 1/10 and 1/3 of the polluted air, preferably about 1/5, the concentration of the organic compounds decomposed in the photooxidation process has been reduced to a preferred level, i.e. the pollutants remaining in the combined air flow, after said combined air flow has passed the air particle filter, e.g. the electrostatic precipitator, has been reduced to concentrations which is acceptable to submit into the surroundings. However, a sub-flow of about 2/3 of the polluted air is also contemplated within the scope of the present invention.

In a preferred embodiment the at least one UV-lamp is an excimer lamp. Excimer lamps are quasi-monochromatic light sources available over a wide range of wavelengths in the ultraviolet (UV) and vacuum ultraviolet (VUV) spectral regions. The operation of excimer lamps is based on the formation of excited dimers (excimers). These excimer formations are unstable and will disintegrate within nanoseconds, giving up their excitation (binding) energy in the form of photons (radiation) at a characteristic wavelength.

Since only a single gas is used in an excimer lamp, the radiation output by the excimer lamp is restricted to a narrow UV wavelength range. This allows a perfect match with the absorption spectrum of the pollutants/compounds that are to be removed from the air, i.e. the excimer lamp in the air treatment unit may be selected in order to match the absorption spectrum of the pollutants in the air to be treated. If desired several excimer lamps emitting different wavelength may be placed in the air treatment unit.

In a preferred embodiment according to the present invention, the excimers are produced using the rare gases, i.e. $He_2$, $Ne_2$, $Ar_2$, $Kr_2$ and $Xe_2$, or the rare gas halides (e.g. ArF, KrF, XeCL and XeF). However, halogens and mercury halogen mixtures (e.g. HgCl, HGBr og HgI) are also contemplated within the scope of the present invention.

The wavelength of the emitted photons depends on the gas used to provide the excimer. This means that different wavelengths of the photons and be obtained by selecting an excimer lamps with the gas of interest. For instance, a xenon excimer lamp will generate radiation with a wavelength of 172 nm, whereas an argon excimer lamp will provide a wavelength of 129 nm and a krypton fluoride excimer lamp will provide a wavelength of 222 nm. A complete list of the relevant wavelength can be found in the literature.

The use of excimer lamps offers a number of advantages, high intensity at a defined wavelength, no-self absorption, and flexibility in the construction of the air treatment system according to the present invention. Furthermore, excimer lamps only generate little heat, making them highly suitable for air-condition and/or ventilation purposes, as cooling is not required before the treated air may be submitted into the surroundings. The system according to the invention may accordingly be used at room temperature, i.e. around 10-40° C., preferably around 20-25° C.

In addition, excimer lamps have a long lifetime because the electrodes are not in direct contact with the discharge gases and will thus avoid any corrosion during the discharge process and no contamination of the excimer gas, as is often the situation in conventional mercury lamps leading to a short operating lifetime. Finally, non-toxic materials are used in the excimer lamps and thus inherently, there is no environmental problem.

It is preferred that excimer lamps used in the present invention emits photons having a wavelength in the range between 126 nm and 240 nm, since photon emitted in this range not only will ensure a substantially complete removal of pollutants, but also that the generation of further pollutants, such as NOx, is prevented.

In one advantageous embodiment, the at least one excimer lamp emits a wavelength of about 172 nm. The inventors of the present invention have shown that this wavelength in a very energy efficient way is capable of removing substantially all organic compounds e.g. VOC's by means of photolysis, and simultaneously sterilise the air, by inactivating microorganisms and vira. Furthermore, said wavelength will also produce the oxidant ozone, that will proceed to oxidise organic contaminants present in the air.

In a preferred embodiment the air treatment unit is preferably arranged such that polluted air flowing though said unit will flow over the surface of the UV-lamps and/or close to the surface of said lamps, thereby ensuring that at least 90%, preferably at least 95% and even more preferred substantially all the polluted air flowing through the air treatment unit will be exposed to irradiation from the at least one UV-lamp.

This may e.g. in a preferred embodiment be obtained by ensuring that the at least one UV-lamp is placed close to the walls of the air treatment housing, such that air passing close to said walls will also be exposed to the emitted photos. The direct distance between the walls of the unit and the surface of the UV-lamps is preferably below 2 cm, preferably below 1.5 cm and more preferred below 1 cm.

If more than one UV-lamp is placed in the air treatment unit, said UV-lamps is preferably also placed in close proximity to each other in order to ensure a large emission area, and that substantially all air to be treated in subjected to the emitted UV-light. The inventors of the present invention have shown that this is achieved when the direct (i.e. shortest) distance (taken in a cross-section) between the surface of two adjacent UV-lamps is below 4 cm, and preferably even lower, such as below 2 cm or more preferred below 1 cm.

In order to extend the reaction time in the air treatment unit, it is preferred that system is arranged for passing the sub-flow through the air treatment unit with a lower flow rate than the flow rate of the polluted air that enters/passing though, the air treatment system. Such an arrangement will effectively ensure that the UV-light will get in contact with substantially all pollutants in the air and effectively clean/treat said air, as the emitting irradiation will initiate a photolysis process in the air, and/or ensure that ozone will be generated from oxygen present in the air.

Since the major part of the polluted air by-passes the air treatment unit, and only has to pass over the air particle filter, e.g. the electrostatic precipitator, which does not involve large pressure drops etc, large volumes of air can be efficiently treated using the air treatment system according to the invention.

The inventors of the present invention have found that if the flow rate of the sub-flow is about ⅕ of the flow rate of the polluted air entering the system, the concentrations of the gas-pollutants in the combined air will be reduced to acceptable levels. As an example can be mentioned that if the flow rate of the polluted air is 250 $m^3/h$, the flow rate of the sub-flow is 50 $m^3/h$.

The respective flow rates can easily be adjusted by conventional means. As an example can be mentioned that if the flow of the polluted air is controlled by a first fan and the flow of the sub-flow is controlled by a second fan located in the air treatment unit, the speed of said two fans can be adjusted to the desired flow rate. Alternatively, a single fan can be used, and the flow rate be regulated by means of e.g. air tubes having different dimensions in order to regulate the different flow rates, strategically placed baffles and/or other known means for regulating the flow rate. The fan for regulating the flow of the system may either be placed at the inlet of the system or at the outlet of the system, the only requirement being that the fan can suck air into the system and expel it after treatment. If the air treatment unit also comprises a fan, said fan may also be placed at the inlet or outlet of said unit.

If the at least one UV-lamp is elongated and said UV-lamp is arranged in the air treatment unit in its longitudinal direction substantially parallel to the air flow direction, this will not only increase the period which the sub-flow is subjected to irradiation from the UV-lamp, but also has the advantage that the at least one UV-lamps will not substantially obstruct the air flow.

In order to ensure an even more efficient air cleaning of the polluted air, the system according to the invention may preferably comprise means for recycling the air though said system. This is especially relevant if the polluted air is indoor air e.g. in a home, office or in an air plane, in which pollutants continuously is added to the air. Recycling the air thought the air treatment system according to the invention, will ensure that gas-pollutants and particles continuously are removed from the air.

In a preferred embodiment the air treatment system is a HVAC system, in which an air treatment unit is incorporated into said system upstream of an air particle filter, e.g. an electrostatic precipitator, e.g. in a duct of the HVAC system. i.e. the duct of the HVAC system becomes part of the system according to the invention. It is in this respect preferred that the air treatment unit is an individual unit that easily can be placed in said duct system of the HVAC system.

Existing HVAC systems comprises means for circulating air e.g. heated or cooled, from the air treatment system and return it back to the air treatment system, and if the air treatment unit is placed in such a conventional HVAC system, an especially simple and inexpensive system according to the invention is provided.

A person skilled in the art will understand that the system according to the invention may comprise further means for treating the air, e.g. a mechanical filter, but it is preferred that such additional means does not provide a pressure drop during operation.

The present invention also relates to a method of treated polluted air, preferably using the air treatment system according to the present invention, said method comprises the consecutive steps of:

passing a sub-flow of the polluted air through an air treatment unit comprising at least one UV-lamp, combining the treated sub-flow with the polluted air, and passing the combined air flow over an air particle filter, such as an electrostatic precipitator.

This will, as already described provide an effective degradation of both particles and organic pollutants, and accordingly provide a sufficient removal of the pollutants in the contaminated air before being submitted into the surroundings.

In a modified embodiment, the polluted air is pass over the air particle filter (electrostatic precipitator) before a sub-flow enters the air treatment unit, or alternatively the polluted air and the combined air flow will both be passed over an air particle filter (electrostatic precipitator), i.e. an air particle filter placed upstream and/or downstream of the air treatment unit.

BRIEF DESCRIPTION OF THE DRAWINGS

The invention will be explained in greater detail below, describing only exemplary embodiments of the exhaust gas treatment system and method with reference to the sole drawing, in which FIG. 1 schematically shown a first and preferred embodiment of an air treatment system according to the invention, FIG. 2 schematically shown a second embodiment of an air treatment system according to the invention, and FIG. 3 schematically shown a third embodiment of an air treatment system according to the invention.

The invention will be described below with the assumption that the air treatment system is a HVAC system, and that the air particle filter is an electrostatic precipitator. However, this assumption is not to be construed as limiting, as the system also could be used as a stand alone system, and/or the air particle filter could be any other kind of conventional air particle filter.

DETAILED DESCRIPTION OF SPECIFIC EMBODIMENTS

Figure 1:
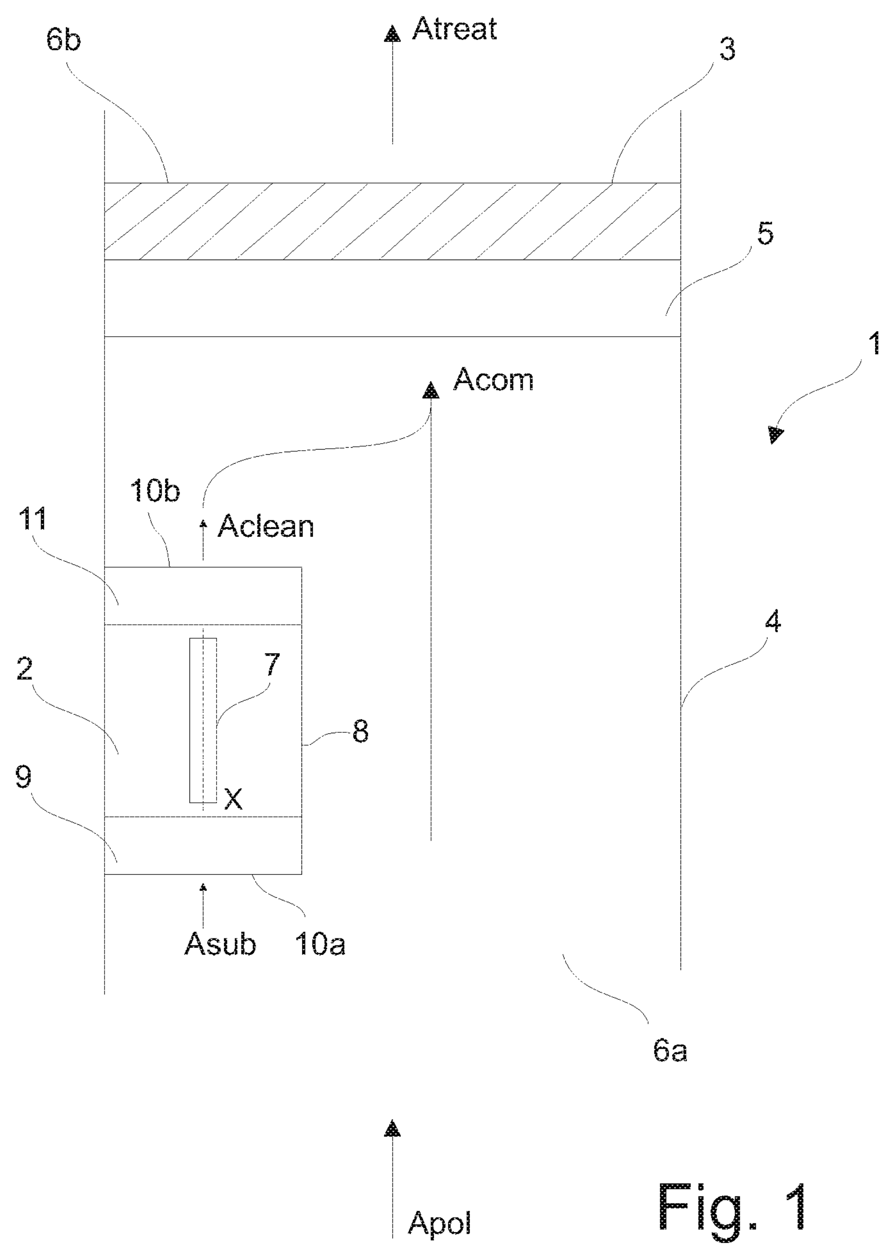

FIG. 1 shows a simplified embodiment of an air treatment system 1 according to the invention. The system 1 comprises an air treatment unit 2 placed upstream of an electrostatic precipitator 3 in an air duct 4 of a HVAC system; a fan 5 is arranged at the outlet for sucking/drawing polluted air $A_{pol}$ into the system at a first end 6*a* of the duct/system, and blow treated air $A_{treat}$ out of the other end 6*b* of the duct/system 1.

The air treatment unit 2 comprises an UV-lamp 7 placed in close proximity to the walls 8 of the unit 2, a fan 9 for sucking a sub-flow $A_{sub}$, of the polluted air $A_{pol}$ into a first end 10*a* of the unit 2 and for expelling clean sub-flow $A_{clean}$ at the other end 10*b* of said unit, and a catalyst 11 arranged for decomposing excess ozone to oxygen.

The UV-lamp 7 is an elongated cylindrically tube having a longitudinal axis X arranged in the flow direction of the air treatment unit (illustrated by arrows). i.e. the air will flow along the length of the UV-lamp 7, thereby ensuring that the sub-flow $A_{sub}$ that enters the unit 2 has the longest possible contact time with the UV-lamp 7 and accordingly the UV-light emitted from said lamp.

The speed of the two fans 5, 9 are adjusted such that the sub-flow $A_{sub}$ is passed thought the air treatment unit 2 with a lower flow rate than the flow rate of the polluted air $A_{pol}$ passing though the air treatment system 1. Such an arrangement will effectively ensure that the UV-light will get in contact with substantially all contaminates in the subflow $A_{sub}$ and effectively clean/treat said sub-flow, as the emitting irradiation will initiate a photooxidation process in the air, and/or ensure that ozone will be generated from oxygen present in the air.

Even thought the fans 5,9 is placed at the outlet of the system 1 and the inlet of the air treatment unit 2 in FIG. 1, a person skilled in the art will understand that one or both fans also could be placed at any another suitable position.

Even though the photooxidation process will basically remove organic pollutants e.g. VOCs from the sub-flow $A_{sub}$, the photooxidation process is so efficient that the overall content of the organic pollutants of the combined air flow $A_{com}$, i.e. in the air-flow after the air $A_{treat}$ that has been treated in the air treatment unit 2 is combined with the remained of the polluted air $A_{pol}$, is significantly reduced.

Since the major part of the polluted air $A_{pol}$ by-passes the air treatment unit 2, and only has to pass the electrostatic precipitator 3, which does not involve large pressure drops etc, large volumes of air can be treated using the air treatment system 1 according to the invention in a fast and effective manner.

As the air treatment unit 2 in the embodiment shown is placed in a HVAC system, it is preferred that the air treatment unit 2 is an individual unit that easily can be retrofitted in the duct system 4 of the HVAC system.

Existing HVAC systems will comprise means for recycling the air though said system, which is relevant if the polluted air is indoor air e.g. in a home, office or in an air plane, in which pollutants continuously is added to the air. Recycling the air thought the air treatment system according to the invention, will therefore ensure that low levels of both gas-pollutants and particles continuously will be maintained.

The UV-lamp used in the present invention may be any UV-lamp capable of initiating a photooxidation process. However, in a preferred embodiment the at least one UV-lamp is an excimer lamp, which offers a number of advantages, high intensity at a defined wavelength, no-self absorption, and flexibility in the construction of the air treatment system according to the present invention. Furthermore, excimer lamps only generate little heat, making them highly suitable for air-condition and/or ventilation purposes, as cooling is not required before the treated air may be submitted into the surroundings FIG. 1 only shows the use of a single UV-lamp, however a person skilled in the art will understand that the air treatment unit may comprise two, or more UV-lamps if a larger UV-emission area is desired or if the UV-lamps are arranged for emitting different wavelengths. Accordingly, the system according to the invention can be adapted to be used in both large-area industrial applications and for domestic uses.

Furthermore, a person skilled in the art will understand that even thought a catalyst is preferred in the system according to the invention, said catalyst can be omitted in the embodiment of FIG. 1.

Figure 2:
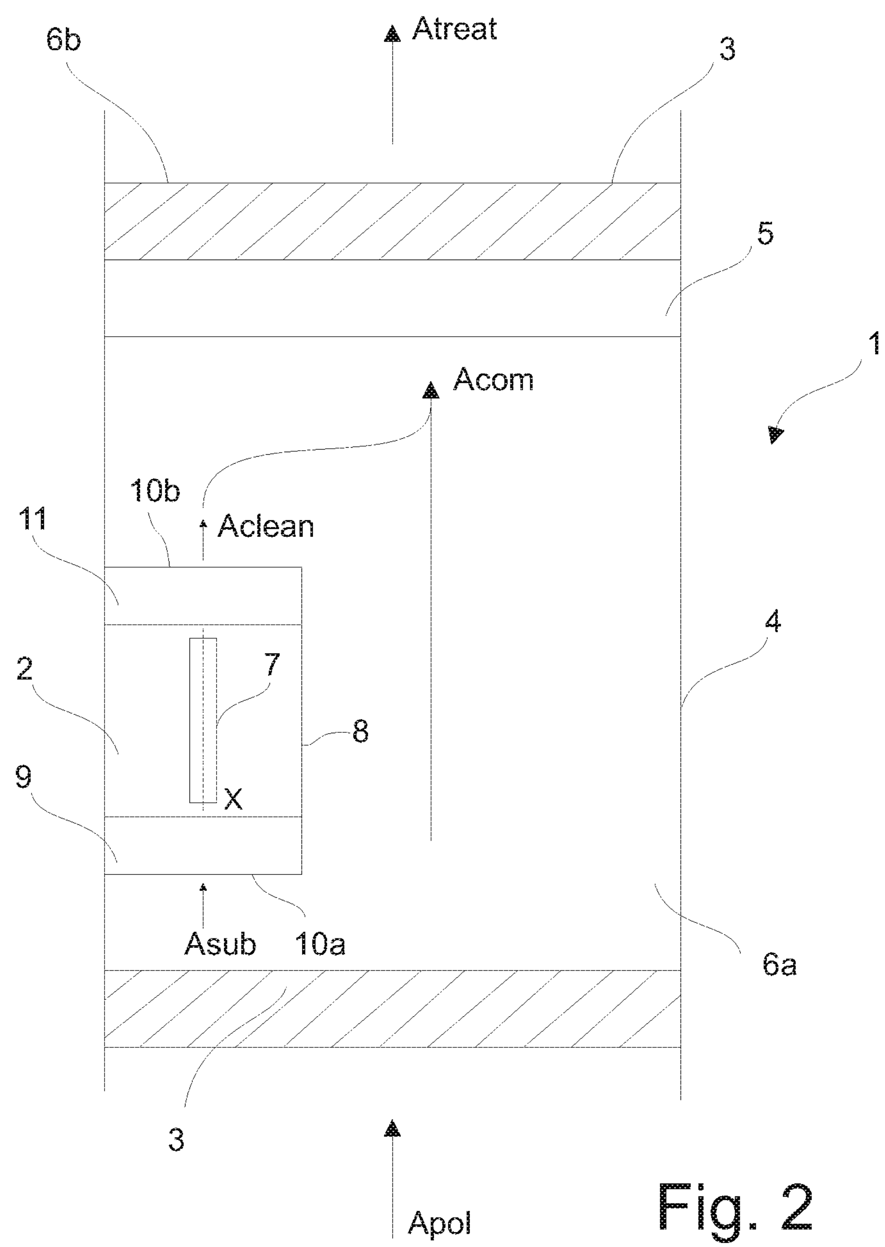
Figure 3:
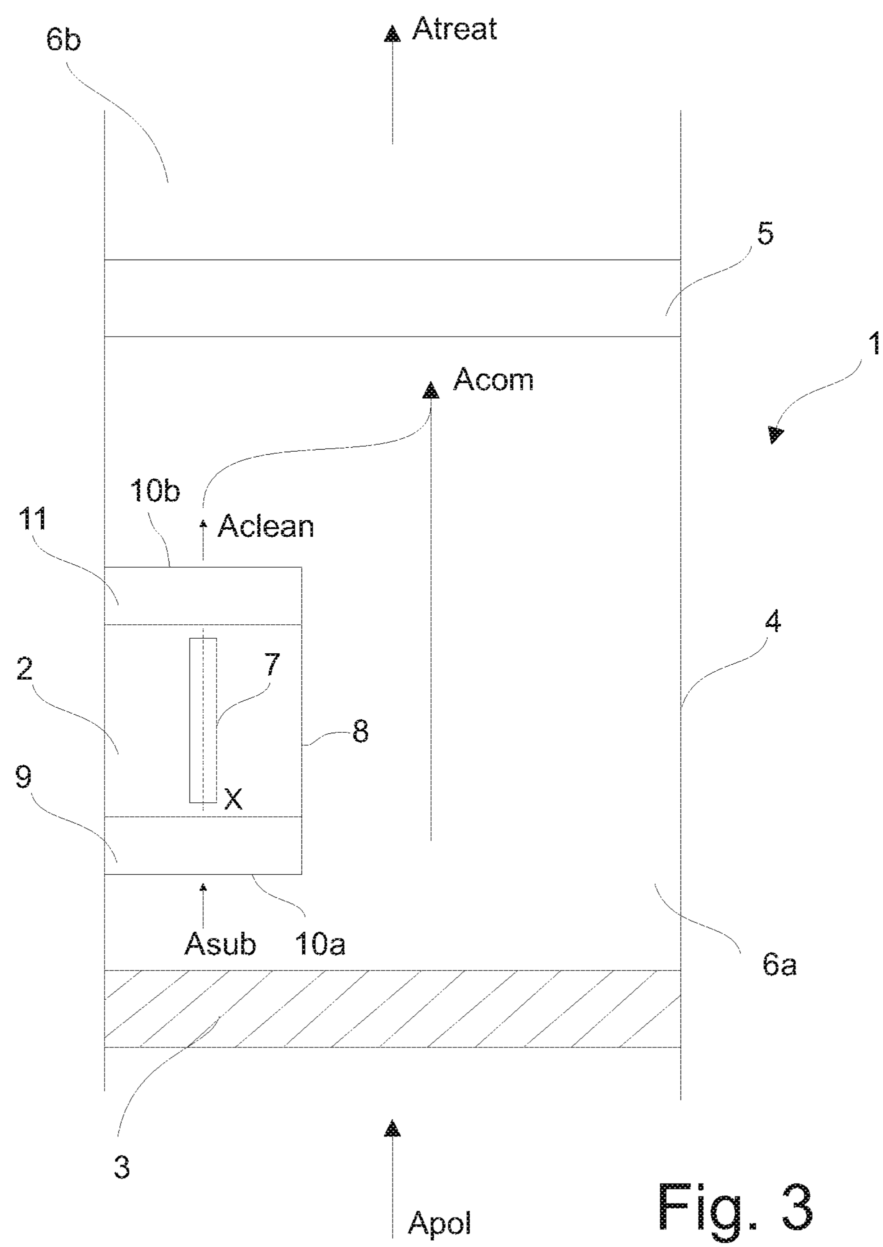

Alternative embodiments are shown in FIGS. 2 and 3, these embodiments correspond to the embodiment shown in FIG. 1, with the modification of the placement of the electrostatic precipitator 3. The embodiment shown in FIG. 2 comprises two electrostatic precipitators 3, one placed before the air treatment unit and one placed after said unit. In the embodiment of FIG. 3 the electrostatic precipitators 3 is placed before the air treatment unit, seen in the flow direction.

Modifications and combinations of the above principles and designs are foreseen within the scope of the present invention.

The invention claimed is:

1. An air treatment system arranged for treating polluted air ($A_{pol}$) at least by means of an air particle filter, said system comprises at least one duct and a fan for directing air though the air treatment system and expelling it after treatment, wherein said air treatment system comprises an air treatment unit comprising at least one UV-lamp, said air treatment unit being placed upstream of the air particle filter and being arranged for directing a sub-flow ($A_{sub}$) of the polluted air ($A_{pol}$) through said air treatment unit and for subjecting only said sub-flow to photooxidation, and wherein the system is arranged such that the sub-flow, after being subjected to photooxidation in the air treatment unit, is combined with the polluted air that bypass the air treatment unit and the combined air-flow is then passed over the air particle filter that is placed after the air treatment unit seen in the flow direction.

2. The air treatment system according to claim 1, wherein the air treatment unit comprises at least one catalyst, and wherein said catalyst is adapted for treating the air as a photocatalyst, or reduce the concentration of submitted ozone into the surroundings.

3. The air treatment system according to claim 1, wherein the sub-flow ($A_{sub}$) directed though the air treatment unit is between 1/10 and 2/3 of the polluted air ($A_{pol}$).

4. The air treatment system according to claim 1, wherein the UV-lamp is an excimer lamp arranged for emitting a wavelength in the range between 126 nm and 240 nm.

5. The air treatment system according to claim 1, wherein the air treatment unit comprises an air treatment housing with walls, and wherein the direct distance between the walls of the unit and the surface of the UV-lamps is below 2 cm whereby the sub-flow ($A_{sub}$) flowing though said unit will flow over the surface of the at least one UV-lamp and/or close to the surface of said lamp, thereby ensuring that at least 90% of the sub-flow will be exposed to irradiation.

6. The air treatment system according to claim 1, wherein the system is arranged for passing the sub-flow ($A_{sub}$) through the air treatment unit with a lower flow rate than the flow rate of the polluted air ($A_{pol}$) entering into the air treatment system.

7. The air treatment system according to claim 1, wherein the flow rate of the sub-flow ($A_{sub}$) is about 1/5 of the flow rate of the polluted air ($A_{pol}$).

8. The air treatment system according to claim 1, wherein the air treatment system is configured to recycle the air though said system.

9. The air treatment system according to claim 1, wherein the air treatment system is a heating and/or ventilation and/or air conditioning system comprising an electrostatic precipitator and the air treatment unit is a separate unit placed in a duct of said heating and/or ventilation and/or air conditioning system upstream of the electrostatic precipitator.

10. The air treatment system according to claim 1, wherein the air particle filter is an electrostatic precipitator.

11. Use of an air treatment system according to claim 1 for treating a contaminated air steam comprising pollutants in the form of particles and organic compounds, such as VOCs.

12. A method of treating polluted air using the air treatment system according to claim 1, wherein said method comprises the consecutive steps of:

passing a sub-flow of the polluted air through an air treatment unit comprising at least one UV-lamp, combining the clean sub-flow ($A_{clean}$) delivered from the air treatment unit with the remainder of the polluted air ($A_{pol}$) providing a combined air flow ($A_{corn}$), and passing the combined air flow ($A_{corn}$) over an air particle filter.

13. The method according to claim 12, wherein the sub-flow ($A_{sub}$) is passed thought the air treatment unit with a lower flow rate than the flow rate of the remaining polluted air ($A_{pol}$) and/or the combined air flow ($A_{corn}$).

14. The method according to claim 12, wherein the polluted air is passed through the air particle filter before a sub-flow of said polluted air enters the air treatment unit.

* * * * *